(12) United States Patent
Lattanzio et al.

(10) Patent No.: US 9,381,301 B2
(45) Date of Patent: Jul. 5, 2016

(54) SYSTEMS AND METHODS FOR MONITORING AND CONTROLLING INTERNAL PRESSURE OF AN EYE OR BODY PART

(75) Inventors: Frank A. Lattanzio, Cheaspeake, VA (US); Thomas C. Delahanty, Thousand Oaks, CA (US)

(73) Assignee: Eastern Virginia Medical School, Norfolk, VA (US)

( * ) Notice: Subject to any disclaimer, the term of this patent is extended or adjusted under 35 U.S.C. 154(b) by 938 days.

(21) Appl. No.: 12/298,485

(22) PCT Filed: Apr. 25, 2007

(86) PCT No.: PCT/US2007/010138
§ 371 (c)(1),
(2), (4) Date: Jun. 15, 2009

(87) PCT Pub. No.: WO2007/127305
PCT Pub. Date: Nov. 8, 2007

(65) Prior Publication Data
US 2009/0275924 A1   Nov. 5, 2009

Related U.S. Application Data

(60) Provisional application No. 60/794,831, filed on Apr. 26, 2006.

(51) Int. Cl.
*A61M 39/22* (2006.01)
*A61M 39/28* (2006.01)
(Continued)

(52) U.S. Cl.
CPC .............. *A61M 5/16804* (2013.01); *A61B 3/16* (2013.01); *A61B 5/076* (2013.01); *A61B 5/4839* (2013.01);
(Continued)

(58) Field of Classification Search
USPC .......... 600/398, 405, 406, 561; 604/540, 541, 604/9
See application file for complete search history.

(56) References Cited

U.S. PATENT DOCUMENTS 4,443,218 A * 4/1984 DeCant et al. .................. 604/67
4,676,772 A * 6/1987 Hooven ............................ 604/9
(Continued)

FOREIGN PATENT DOCUMENTS

DE    3127882 A1 * 2/1983 ............. A61M 1/00
DE    4438201 A1 * 10/1994
(Continued)

OTHER PUBLICATIONS

International Search Report mailed May 30, 2008.
(Continued)

*Primary Examiner* — Sean Dougherty
(74) *Attorney, Agent, or Firm* — Wilmer Cutler Pickering Hale and Dorr LLP

(57) ABSTRACT

Systems and methods for automatically monitoring and controlling pressure in a body part are disclosed. The systems include an implantable tube with one open end of the tube implanted in the body part, an implantable valve coupled with the tube having at least one open state and a closed state, an implantable sensor for measuring pressure, and an implantable control device coupled with the sensor and the valve. The control device switches the valve between the at least one open state and the closed state, based on pressure information received from the sensor. When the valve is in the at least one open state, the tube drains fluids from the body part due to a difference of pressure between the open ends of the tube. Methods for using the systems to administer drugs and monitor and control fluid pressures in various biological systems are also disclosed.

27 Claims, 14 Drawing Sheets

(51) Int. Cl.
| | |
|---|---|
| *A61M 5/168* | (2006.01) |
| *A61B 3/16* | (2006.01) |
| *A61B 5/07* | (2006.01) |
| *A61B 5/00* | (2006.01) |
| *A61F 9/007* | (2006.01) |

(52) U.S. Cl.
CPC ............ *A61F 9/00781* (2013.01); *A61M 39/22* (2013.01); *A61M 39/28* (2013.01); *A61B 2560/045* (2013.01)

(56) References Cited

U.S. PATENT DOCUMENTS

| | | | | |
|---|---|---|---|---|
| 4,688,998 | A * | 8/1987 | Olsen et al. | 417/356 |
| 4,787,886 | A * | 11/1988 | Cosman | 604/9 |
| 4,796,641 | A * | 1/1989 | Mills et al. | 600/561 |
| 5,167,615 | A * | 12/1992 | East et al. | 604/9 |
| 5,433,701 | A | 7/1995 | Rubinstein | |
| 5,637,083 | A * | 6/1997 | Bertrand et al. | 604/9 |
| 5,676,162 | A * | 10/1997 | Larson et al. | 128/899 |
| 6,077,299 | A * | 6/2000 | Adelberg et al. | 623/24 |
| 6,120,460 | A * | 9/2000 | Abreu | 600/558 |
| 6,168,575 | B1 | 1/2001 | Soltanpour | |
| 6,186,149 | B1 * | 2/2001 | Pacella et al. | 128/898 |
| 6,264,625 | B1 * | 7/2001 | Rubenstein et al. | 604/9 |
| 6,336,924 | B1 | 1/2002 | Lecuyer et al. | |
| 6,423,001 | B1 * | 7/2002 | Abreu | 600/405 |
| 6,537,232 | B1 * | 3/2003 | Kucharczyk et al. | 600/561 |
| 6,554,822 | B1 * | 4/2003 | Holschneider et al. | 604/892.1 |
| 6,580,947 | B1 * | 6/2003 | Thompson | 607/30 |
| 6,589,198 | B1 | 7/2003 | Soltanpour et al. | |
| 6,730,123 | B1 * | 5/2004 | Klopotek | 623/6.22 |
| 6,847,847 | B2 * | 1/2005 | Nisch et al. | 607/54 |
| 6,862,433 | B2 | 3/2005 | Callaway, Jr. | |
| 6,915,162 | B2 * | 7/2005 | Noren et al. | 607/23 |
| 6,939,299 | B1 * | 9/2005 | Petersen | A61B 3/16 600/300 |
| 7,037,335 | B2 * | 5/2006 | Freeman et al. | 623/4.1 |
| 7,041,063 | B2 * | 5/2006 | Abreu | 600/549 |
| 7,144,616 | B1 * | 12/2006 | Unger et al. | 428/172 |
| 7,181,287 | B2 * | 2/2007 | Greenberg | 607/116 |
| 7,195,608 | B2 * | 3/2007 | Burnett | 604/9 |
| 7,311,690 | B2 * | 12/2007 | Burnett | 604/9 |
| 7,398,688 | B2 * | 7/2008 | Zdeblick et al. | 73/700 |
| 7,524,298 | B2 * | 4/2009 | Gharib et al. | 604/9 |
| 7,621,886 | B2 * | 11/2009 | Burnett | 604/9 |
| 7,678,065 | B2 * | 3/2010 | Haffner et al. | 600/561 |
| 7,691,051 | B2 * | 4/2010 | Connors et al. | 600/29 |
| 7,708,711 | B2 * | 5/2010 | Tu et al. | 604/8 |
| RE41,394 | E * | 6/2010 | Bugge | A61M 1/127 600/16 |
| 7,909,790 | B2 * | 3/2011 | Burnett | 604/9 |
| 8,025,064 | B2 * | 9/2011 | Connors et al. | 128/897 |
| 8,182,435 | B2 * | 5/2012 | Dacquay et al. | 600/591 |
| 8,206,440 | B2 * | 6/2012 | Guarnieri | 623/4.1 |
| 8,257,295 | B2 * | 9/2012 | Rickard et al. | 604/9 |
| 8,317,770 | B2 * | 11/2012 | Miesel et al. | 604/500 |
| 8,419,673 | B2 * | 4/2013 | Rickard | 604/9 |
| 8,475,374 | B2 * | 7/2013 | Irazoqui et al. | 600/398 |
| 8,545,431 | B2 * | 10/2013 | Rickard | 604/9 |
| 8,585,630 | B2 * | 11/2013 | Meng et al. | 604/8 |
| 8,603,024 | B2 * | 12/2013 | Bohm et al. | 604/9 |
| 8,678,997 | B2 * | 3/2014 | Forsell | 600/38 |
| 8,961,448 | B2 * | 2/2015 | Forsell | B01D 46/0064 604/19 |
| 2002/0013545 | A1 * | 1/2002 | Soltanpour et al. | 604/9 |
| 2002/0022793 | A1 * | 2/2002 | Bertrand et al. | 604/9 |
| 2002/0049374 | A1 * | 4/2002 | Abreu | 600/405 |
| 2002/0052563 | A1 | 5/2002 | Penn et al. | |
| 2002/0116021 | A1 * | 8/2002 | Gordon | 606/167 |
| 2002/0151770 | A1 * | 10/2002 | Noll et al. | 600/300 |
| 2002/0151816 | A1 * | 10/2002 | Rich et al. | 600/547 |
| 2002/0183649 | A1 * | 12/2002 | Reich et al. | 600/561 |
| 2003/0163019 | A1 * | 8/2003 | Goldowsky | 600/16 |
| 2003/0236442 | A1 * | 12/2003 | Connors et al. | 600/29 |
| 2004/0020239 | A1 | 2/2004 | LaForce et al. | |
| 2004/0049105 | A1 * | 3/2004 | Crutchfield et al. | 600/407 |
| 2004/0111050 | A1 * | 6/2004 | Smedley et al. | 604/9 |
| 2004/0124147 | A1 * | 7/2004 | Fissell et al. | 210/650 |
| 2004/0147871 | A1 | 7/2004 | Burnett | |
| 2004/0147906 | A1 * | 7/2004 | Voyiazis et al. | 604/891.1 |
| 2004/0162545 | A1 * | 8/2004 | Brown et al. | 604/541 |
| 2004/0169932 | A1 * | 9/2004 | Esch et al. | 359/665 |
| 2004/0260229 | A1 * | 12/2004 | Meir | 604/9 |
| 2005/0010159 | A1 * | 1/2005 | Reich et al. | 604/8 |
| 2005/0020962 | A1 * | 1/2005 | Reich | A61M 27/006 604/8 |
| 2005/0022403 | A1 * | 2/2005 | Moskowitz et al. | 33/355 R |
| 2005/0038371 | A1 * | 2/2005 | Reich et al. | 604/9 |
| 2005/0049578 | A1 * | 3/2005 | Tu et al. | 604/890.1 |
| 2005/0092335 | A1 * | 5/2005 | Bertrand et al. | 128/899 |
| 2005/0096582 | A1 * | 5/2005 | Burnett | 604/9 |
| 2005/0103114 | A1 * | 5/2005 | Bly et al. | 73/754 |
| 2005/0143814 | A1 * | 6/2005 | Esch et al. | 623/6.22 |
| 2005/0181009 | A1 * | 8/2005 | Hunter et al. | 424/423 |
| 2005/0181010 | A1 * | 8/2005 | Hunter et al. | 424/423 |
| 2005/0182312 | A1 * | 8/2005 | Bruce et al. | 600/399 |
| 2005/0197652 | A1 * | 9/2005 | Nat | 604/891.1 |
| 2005/0205136 | A1 * | 9/2005 | Freeman | 137/554 |
| 2005/0209572 | A1 * | 9/2005 | Rome et al. | 604/250 |
| 2005/0228284 | A1 | 10/2005 | Baumgartner et al. | |
| 2005/0273034 | A1 * | 12/2005 | Burnett | 604/9 |
| 2006/0020239 | A1 | 1/2006 | Geiger et al. | |
| 2006/0030751 | A1 | 2/2006 | Uesugi et al. | |
| 2006/0036208 | A1 * | 2/2006 | Burnett | 604/9 |
| 2006/0058731 | A1 * | 3/2006 | Burnett et al. | 604/29 |
| 2006/0129138 | A1 * | 6/2006 | Nat | 604/891.1 |
| 2006/0155158 | A1 * | 7/2006 | Aboul-Hosn | 600/16 |
| 2007/0100443 | A1 * | 5/2007 | Peyman | 623/6.13 |
| 2007/0106199 | A1 * | 5/2007 | Krivoy et al. | 604/9 |
| 2007/0156079 | A1 * | 7/2007 | Brown | 604/9 |
| 2007/0197957 | A1 * | 8/2007 | Hunter et al. | 604/65 |
| 2007/0282157 | A1 * | 12/2007 | Rottenberg et al. | 600/16 |
| 2008/0139959 | A1 * | 6/2008 | Miethke | A61B 5/0031 600/561 |
| 2008/0288013 | A1 * | 11/2008 | Schecter | 607/23 |
| 2009/0069648 | A1 * | 3/2009 | Irazoqui et al. | 600/302 |
| 2009/0112103 | A1 * | 4/2009 | Kassem | A61B 5/0031 600/488 |
| 2009/0226328 | A1 * | 9/2009 | Morello | 417/1 |
| 2010/0269632 | A1 * | 10/2010 | Dlugoss | 74/732.1 |
| 2011/0066254 | A1 * | 3/2011 | Forsell | 623/23.64 |
| 2012/0289883 | A1 * | 11/2012 | Meng et al. | 604/9 |

FOREIGN PATENT DOCUMENTS

| | | | | |
|---|---|---|---|---|
| DE | 4427583 A1 * | 2/1996 | | A61M 39/00 |
| EP | 1491137 A2 * | 12/2004 | | A61B 5/03 |
| JP | 04069985 A * | 3/1992 | | |
| WO | WO-2004/014218 A2 | 2/2004 | | |
| WO | WO 2004014218 A2 * | 2/2004 | | |

OTHER PUBLICATIONS

European Patent Application No. 07756059 Supplementary Search report (seach completed Mar. 19, 2010) (2 pages).
English Translation of Notice of Reasons for Rejection mailed May 17, 2012 by Japanese Patent Office for corresponding Japanese Patent Application No. 2009-507800 (2 pages).

* cited by examiner

SYSTEMS AND METHODS FOR MONITORING AND CONTROLLING INTERNAL PRESSURE OF AN EYE OR BODY PART

FIELD OF THE INVENTION

Embodiments of the present invention relates to new and useful apparatus, systems and methods for monitoring and controlling pressure in body cavities, tissues and organs in living systems and, more particularly, to intraocular pressure sensor and valve apparatus, systems and methods of using them. Embodiments of the present invention may also be used to administer drugs and/or other agents to living or non-living systems by controlling fluid access to an implanted or remote reservoir.

BACKGROUND OF THE INVENTION

Primary open-angle glaucoma (POAG), a widespread, chronic disease, is classified by the World Health Organization as the third leading cause of blindness. As many as 67 million people suffer from glaucoma and 10% will lose vision in both eyes as a result. Even in developed countries with advanced medical care, fewer than half of those with glaucoma associated with clinically elevated intraocular pressure (IOP) are even aware of their condition.

The primary clinical feature of glaucoma is progressive damage to the optic nerve with the attendant loss of visual function. Although the mechanism for glaucomatous optic neuropathy is uncertain, elevation of IOP is considered a primary risk factor. As early as 1907, physicians recognized that control of IOP slowed the progression of the disease. Studies have shown that decreasing IOP to <18 mm Hg decreases the risk of developing glaucoma by 50%, and, in patients with glaucoma, halts the progression of visual field effects. Even patients with so called normal-tension glaucoma benefit from a reduction in IOP.

Therefore, IOP has become a surrogate, easily measured endpoint to define successful therapeutic interventions, both pharmacologic and surgical. These therapeutic interventions do not treat glaucoma directly. Instead they attack one of the most important risk factors, namely elevated IOP. Both drugs and surgical approaches effectively decrease IOP and minimize visual field loss. This implies that it is the decrease in IOP, and not the method of achieving it, that preserves visual function. However, drugs and surgically implanted passive valves have their own limitations.

To decrease IOP, most drugs either increase outflow of aqueous humor from the anterior chamber of the eye, e.g., prostaglandin $F_{2\alpha}$, or decrease its production, e.g., beta-adrenergic blockers and carbonic anhydrase inhibitors. Some drugs, such as alpha-adrenergic agonists, do both. Their effects vary depending upon the patient's compliance, the patient's physiology and biochemistry, pathological condition, presence of other drugs and other changes in the environment that can affect IOP.

Like hypertension, elevated IOP is not detected by the patient until end organ damage becomes apparent, in this case glaucomatous optic neuropathy. Since patients cannot detect an immediate benefit, their motivation to administer the drugs is lacking and patient compliance is often poor. In addition, drugs, even those applied topically, often cause adverse effects, are uncomfortable to apply in the eye, and present a significant, continuing expense.

Although the reduction of IOP by surgical methods also effectively reduces progression of visual defects, long-term control is rarely achieved. Existing approaches such as laser trabeculoplasty, trabeculectomy, and implantable valves require surgical implementation, have set points that cannot be controlled once implanted, and generally have variable control of IOP that can depend on rates of healing, aqueous humor production and other confounding factors. Although patient compliance is not a factor here, the surgical approach is often of limited effectiveness due to formation of fibrous scar tissue and may predispose patients to cataracts. In addition, when compared to medical therapy, surgical patients reported a slightly higher incidence of long term ocular burning, redness and dry eye.

A major limitation of existing approaches to treatment is that neither drugs nor surgical procedures are capable of automatically adjusting their actions based on the patient's IOP. This drawback is of particular concern because maintenance of IOP in POAG below 18 mm Hg is generally considered essential to decrease the onset of glaucomatous optic neuropathy (or, once established, prevent its progression). Normal-tension glaucoma patients typically require a lower set point of less than 11 mm Hg. In addition, the lack of adjustment further limits the utilization of any other drugs that may elevate or decrease IOP as one of their primary or side effects.

One method for treating glaucoma is to devise an artificial drainage shunt with a pressure-sensitive valve that allows aqueous humor to flow from the anterior chamber of the eye. However, existing valve-regulated devices are limited. Conventional valves are passive devices that often allow too little or occasionally too much drainage of aqueous humor. Another disadvantage is the inability to actively monitor IOP on a long-term basis. In addition, conventional devices, even when working optimally, cannot be adjusted once in place, which leaves the patient and the physician at the mercy of pre-existing valve parameters. Furthermore, these valves may fail and, therefore, must be removed due to poor control in terms of proper pressure regulation.

Therefore, there is a need for an automated system that will permit flexible and long-term monitoring and control of IOP in glaucoma patients. There is also a need for more efficient and consistent regulation of pressure for other biomedical or commercial applications. The present invention is directed to these and other ends.

SUMMARY OF THE INVENTION

The present invention provides systems and methods for monitoring and controlling pressure of a body part, for example IOP, by automatically measuring the pressure and controlling a valve and a sensor. Systems of the present invention permit constant monitoring and control of pressure (e.g., IOP), with the pressure set point of the system adjustable by a physician or a patient. Data from the valve and sensor may be recorded and transmitted to the physician or patient to determine that the clinically selected pressure is being maintained and that the valve is functioning properly.

The present invention has a number of advantages compared to conventional therapies. There is no concern about patient compliance, drug side effects or drug interactions. Control of pressure is maintainable and not affected by normal physiological changes, or, for that matter, by changes that may occur due, for example, to drug administration or changes in pathology. Preferred embodiments of the present invention are capable of monitoring their own performance and adjusting for changes in liquid flow in a body part (e.g., aqueous humor flow in an eye or cerebrospinal fluid in the brain) and other variables that might affect pressure in the body part. The devices of the present invention can, in preferred embodiments, inform the care-giver of any problems related to pressure immediately, with the result that any acute or chronic pressure-mediated damage that might occur with other devices or drugs may be reduced or prevented. In addition, the apparatus and systems of the present invention can accommodate the use of larger orifices, to prevent device clogging, while avoiding undesirable loss of pressure (e.g., IOP) inside a body part. Preferred systems of the present invention may also have a fail-safe mode for adjusting valve function.

Systems for automatically monitoring and controlling pressure of a body part (e.g., IOP) are disclosed. In some embodiments, the systems include an implantable tube having a first open end and a second open end, where the first open end is disposed in the body part (e.g., an anterior chamber of an eye). The systems also preferably include an implantable valve coupled with the tube, the valve having one or more open states and a closed state. In addition, the systems preferably include an implantable sensor configured obtain at least one measurement of pressure within the body part (e.g., IOP), and an implantable control device coupled with the sensor and the valve. The control device is configured to receive the pressure measurement and switch the valve between the one or more open states and the closed state accordingly. When the valve is in the one or more open states, the tube drains liquid from the body part (e.g., aqueous humor from the anterior chamber of an eye) due to a difference of pressure between the first and the second open end of the tube. In some embodiments, the systems further include an implantable pump configured to deliver drugs from a reservoir into the body part.

The implantable sensor that is preferably included in the systems can be a piezoresistive transducer, or other types of sensors, for example a fiber optic sensor. In one embodiment, the sensor is further configured to obtain a temperature measurement, and the control device is further configured to receive the temperature measurement and switch the valve based on the pressure and the temperature measurements.

In some embodiments, the valve can be switched between the at least one open state and the closed state by an external magnet. In one embodiment, the valve include at least one electromagnet, and the control device switches the valve between the at least one open state and the closed state by polarizing the at least one electromagnet. The valve can further include an implantable sleeve having a first end and a second end both made from a material that is reactive to magnetic force, an implantable blade inside the sleeve having a first magnetic end and a second magnetic end, and an additional sensor, such as an optical, proximity, or contact sensor, for verifying the position of the blade. The position of the blade determines whether the valve is in the one or more open states or the closed state. In one embodiment, the valve includes a rotating member having one or more orifices. In some embodiments, the valve has at least two open states and drains fluids within a body part at different rates in different open states.

In some embodiments, the control device includes a wireless communication module for transmitting information to an external device. The control device may also include a two-way wireless communication module for transmitting and receiving information to and from an external device. In one embodiment, the control device switches the valve between the one or more open states and the closed state according to at least one set point which is configurable by the external device. In some embodiments, the control device can include a battery and an electromagnetic induction system configured to recharge the battery.

Methods of monitoring and controlling pressure of a body part (e.g., IOP) are also disclosed. In some embodiments, the methods include automatically measuring pressure within a body part and automatically determining whether pressure needs to be reduced. This determination can be based on at least one measurement of pressure and at least one set point. The methods also include automatically releasing fluids from a body part (e.g., aqueous humor from an anterior chamber), thereby reducing pressure of the body part, upon determining that pressure needs to be reduced. The methods can further include automatically recording a plurality of pressure measurements.

In some embodiments, determining whether pressure needs to be reduced is performed by automatically comparing the at least one measurement of pressure with a low set point and a high set point. In one embodiment, releasing fluids includes automatically releasing fluids from the body part at a first rate upon determining that the at least one measurement is above the high set point, and automatically releasing fluids from the body part at a second rate upon determining that the at least one measurement is below the high set point and above the low set point, where the first rate is faster than the second rate.

Embodiments of the present invention can also be used to elevate pressure of a body part and/or to administer drugs to a body part. For example, if intraocular pressure needed to be chronically elevated, outflow tract capacity of an eye could be pharmacologically or surgically reduced, and/or aqueous humor production can be pharmacologically increased. Then the pressure control system of the present invention can be used to maintain IOP at a certain level. The system can also be used to administer drugs by granting access to an implanted or remote reservoir in response to changes in pressure within the eye or other cavity or organ.

BRIEF DESCRIPTION OF THE DRAWINGS

The Detailed Description of the Invention, including the description of various embodiments of the invention, will be best understood when read in reference to the accompanying figures wherein.

DETAILED DESCRIPTION OF THE INVENTION

The present invention provides systems and methods for monitoring and controlling pressure of a body part. Pressure control systems of various embodiments of the present invention are described in connection with FIGS. 1-10 and 12-13. Methods for controlling pressure of various embodiments of the present invention are described in connection with FIGS. 11 and 14.

Figure 1:
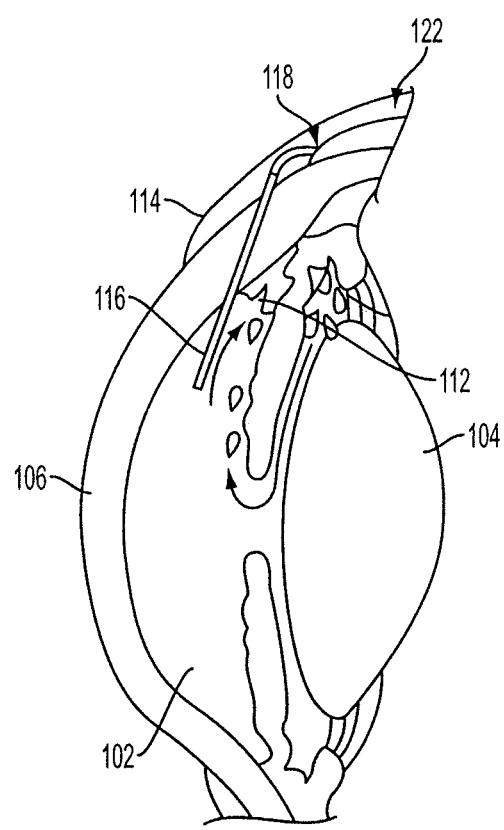
FIG. 1 is a cross-sectional view depicting a portion of a human eye and a pressure control system according to various embodiments of the present invention.

FIG. 1 is a cross-sectional view depicting a portion of a human eye and a pressure control system 118 of various embodiments of the present invention. An anterior chamber 102 of the eye contains aqueous humor, which normally flows out of the eye through channel 112. In glaucoma patients, this normal flow is impeded, leading to a buildup of intraocular pressure. To prevent this, system 118 can be implanted to monitor intraocular pressure, and to drain aqueous humor from anterior chamber 102 when desired.

As shown, system 118 includes a tube 116 and a drainage plate 122 coupled with tube 116. One end of the tube can be implanted into anterior chamber 102. In some embodiments, plate 122 is implanted under the conjunctiva 114 of the eye. Alternatively, plate 122 or various components of plate 122 can be implanted at other locations, for example, in the lens 104, in which case aqueous humor is redirected to a blood vessel bed or other systems with the capacity to remove it from the anterior chamber.

System 118 can also be used in combination with or include a drug delivery system for delivering drugs to a body part such as anterior chamber 102. For example, system 118 can include a pump connected with an external or internal drug reservoir. When pressure is low, system 118 can use the pump to deliver drugs to increase the amount of fluid in the anterior chamber 102.

Figure 2:
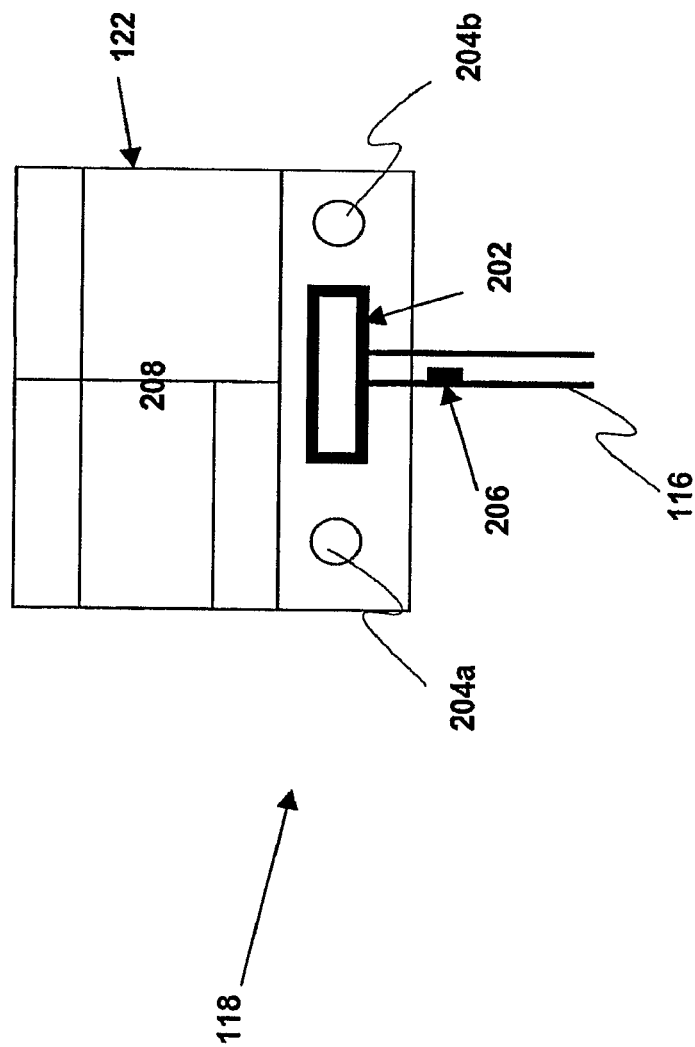
FIG. 2 is a diagram depicting a pressure control system according to various embodiments of the present invention.

FIG. 2 is a diagram further illustrating pressure control system 118 of various embodiments of the present invention. As shown, system 118 includes tube 116, sensor 206, valve 202, and control device 208. Valve 202 is coupled with tube 116. Sensor 206 is disposed within tube 116, but can also be positioned elsewhere. For example, sensor 206 can be built into plate 122. In some embodiments, valve 202 and control device 208 can both be built into plate 122 and sealed to prevent leakage. Alternatively, control device 208 may be separate from plate 122 and implanted at other positions of a body part. Two or more suture anchoring loops 204a and 204b are located on plate 122. The anchoring loops 204a and 204b permit surgical attachment of plate 122 to a body part (e.g., an eye).

System 118 includes a power source (not shown) to provide electric power to sensor 206, valve 202, and control device 208. The power source can be built into plate 122, and can be, for example, a thin film lithium-ion battery having a size of 10 mm×10 mm×0.75 mm. Such a battery can have, for example, a capacity of 2 milliamp hours, and a charging rate of 50 times the discharge rate. Such a battery can also be recharged 100,000 times. System 118 can be designed to have low power consumption so that it can be operated on the battery described above, for at least 24 hours without recharging the battery. Recharging the battery can, for example, take less than 15 minutes.

An electromagnetic induction mechanism (not shown) can be provided as part of control device 208 for recharging the power source after system 118 is implanted. The induction mechanism can include an induction coil, which matches an induction coil of an external charging system. The external charging system can be designed, for example, to transmit 15 milliamps across about 0.5 inch of air space. The power source, as well as control device 208, can be made from a flexible material.

The power source can include an electrical power production device that uses solar (infrared light), heat, chemical, piezoelectric, and/or combinations of these or other sources to generate electrical power. Depending upon the location of the power source, visible light can also be used to generate power. It is know in the art that heat and chemical based technologies can be used to power low voltage, low current devices.

Components of system 118 can be made from flexible and biocompatible materials such as silicone or plastics. Components of system 118 may also have ceramic, magnetic, and/or metal parts coated in silicone or plastics. Biological materials, for example, collagen, can also be used. Components of system 118 can be cast using silicone liquid and molded. Components of system 118 can also be micromachined from silica or other substrates, and coated with a biocompatible material.

Components of system 118 can be made in small sizes. For example, the battery can have a size of 10 mm×10 mm×0.75 mm, and control device 208 can have a size of 10 mm×10 mm. The overall thickness of system 118 can be made to be less than 2 mm. Valve 202 can be, for example, 7 mm long and have a diameter of 1.5 mm. Therefore, plate 122, with control device 208, valve 202, and a battery sealed inside, can have a size of 10 mm×10 mm×2 mm. As these components are made in smaller sizes, system 118 can be made even smaller. Tube 116, for example, can have an inner diameter of 0.35 mm and an outer diameter of 0.65 mm.

Various components of system 118, including sensor 206, valve 202, and control device 208 are described in more detail as follows, in connection with FIGS. 3-7. Sensor 206 is configured to obtain measurements of pressure of a body part (e.g., IOP). In some embodiments, sensor 206 can be an electrical or optical sensor. For example, sensor 206 can be a Wheatstone Bridge, capacitive, fiber optic sensor. Alternatively, sensor 206 can be a piezoelectric transducer, as illustrated by FIGS. 3 and 4.

Figure 3:
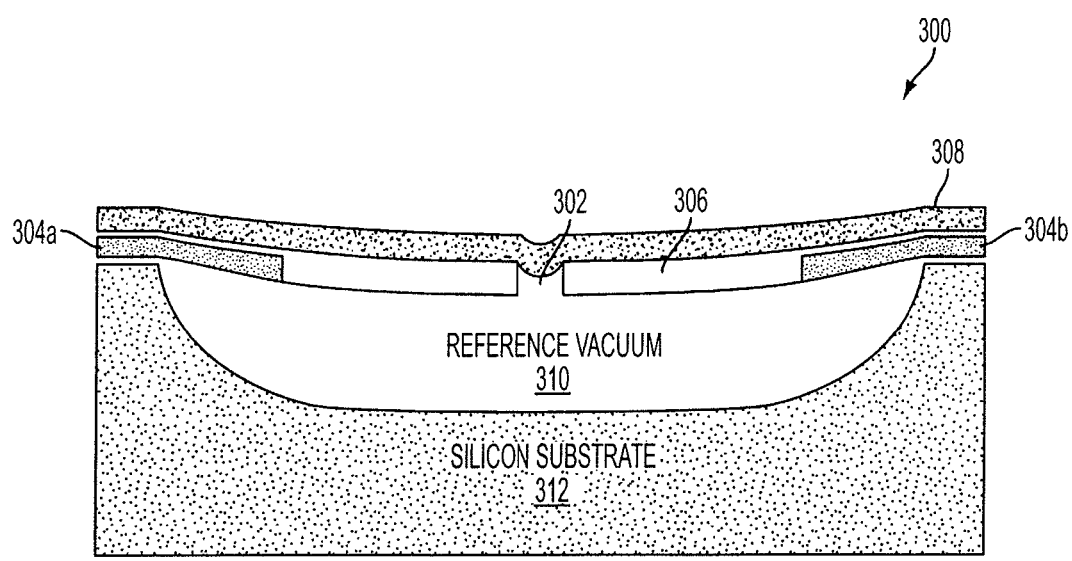
FIG. 3 is a cross-sectional view depicting a pressure sensor, according to various embodiments of the present invention.
Figure 4:
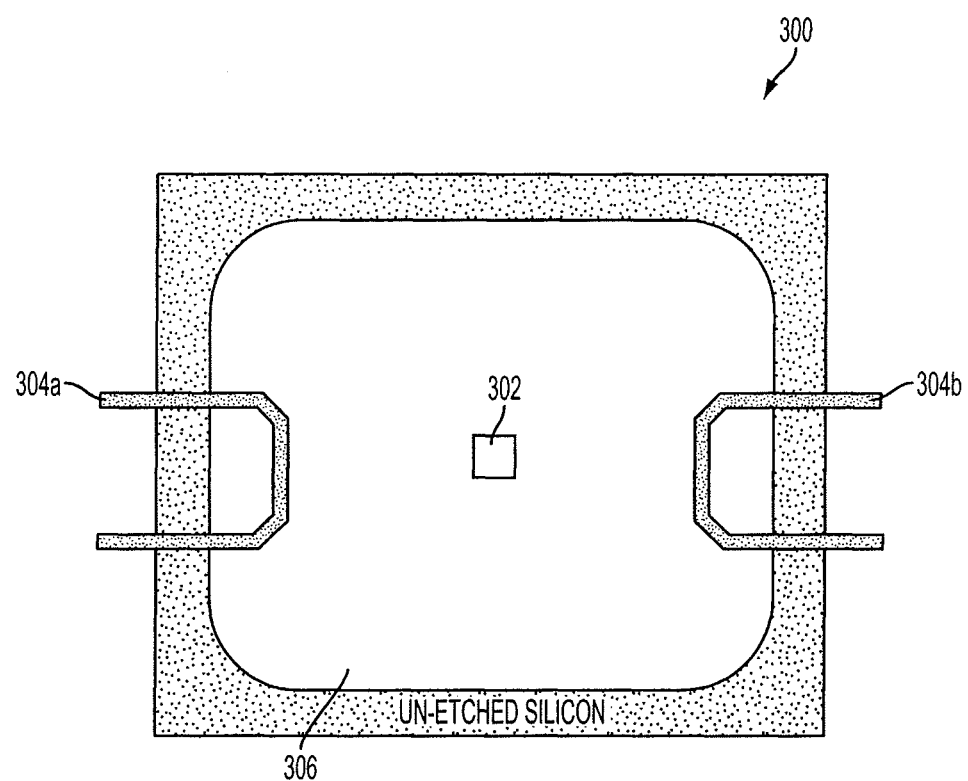
FIG. 4 is a top view depicting a pressure sensor, according to various embodiments of the present invention.

FIG. 3 is a cross-sectional view of the transducer, generally at 300, which shows a reference vacuum 310 enclosed by an oxide membrane 306 and a silicon substrate 312. An etch access hole 302 can be located at the center of membrane 306. Two polycrystalline silicon ("poly") piezoresistors 304a and 304b can be disposed inside membrane 306. A surface passivation and membrane sealant layer 308 seals membrane 306 from the above. As shown in FIG. 4, which is a top view of transducer 300, piezoresistors 304a, 304b can be U-shaped strips disposed at opposite sides of membrane 306.

Transducer 300 uses the piezoresistive effect of the poly piezoresistors 304a, 304b to detect the mechanical flexure of membrane 306 covering hole 302. The size of transducer 300 can be made very small, on the order of hundreds of micrometers or even tens of micrometers. For example, transducer 300 can be can be fabricated using micromachining microelectronic fabrication techniques, with a size of 0.25 mm×0.25 mm×0.25 mm. Such a transducer can also be designed to give a full scale ("FS") reading of 100 mm Hg, giving an accuracy of 1% FS and a drift of less than 1% FS per year.

Using wire-bonding techniques well known in the art, wires can be attached to electrodes on transducer 300, connecting transducer 300 with control device 208. Wires can be coated with Teflon™ materials for electrical isolation. Transducer 300 can be controlled by control device 208 to take pressure measurements repeatedly, and the time intervals between consecutive measurements can be optimized for less power consumption.

Because of the programmable design of system 118, sensor 206 can be recalibrated, which extends the useful life and accuracy of system 118. In some embodiments, sensor 206 can be adjusted to account for corrections due to atmospheric pressure changes (e.g., the patient diving, swimming, or flying in an airplane). A barometric sensor (not shown) that has access to atmospheric pressure can be connected to control device 208 for providing atmospheric pressure information.

In some embodiments, sensor 206 can measure temperature in addition to pressure. For example, piezoelectric transducer 300 illustrated in FIGS. 3 and 4 can be used for such a purpose. Temperature measurements permit temperature correction of the pressure sensor as well as detection of abnormal changes in body temperature. Sensor 206 also can be used to detect changes in heart rate, because pressure of various body parts (e.g., IOP) demonstrates a pulsatile component that follows the heart beat. Therefore, system 118 can be used to administer drugs based on heart rate, temperature or blood pressure changes through the use of an implanted or remote drug reservoir (not shown).

Figure 5A:
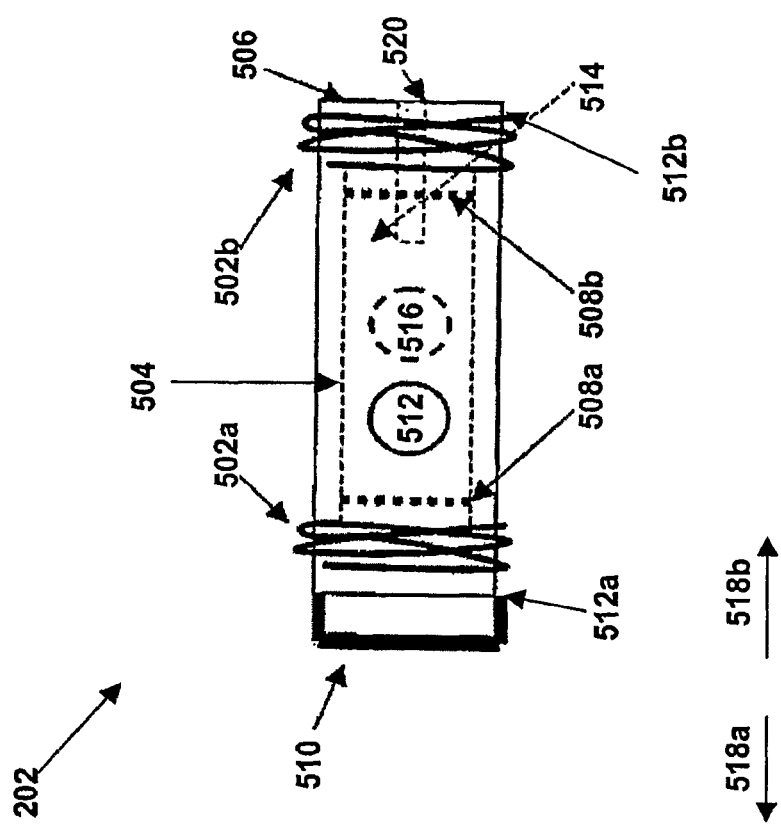
FIG. 5*a* is a perspective view depicting an electromagnetic valve, according to various embodiments of the present invention.

FIG. 5a is a perspective view illustrating a twin magnetic stop, electromagnetic valve 202 of various embodiments of the present invention. Valve 202 includes an outer sleeve 506, which has steel plates 512a, 512b at the two opposite ends, and an orifice 512 between the two ends. Two electromagnets 502a, 502b are located near plates 512a, 512b. A sliding blade 514 with an orifice 516 is positioned inside sleeve 506. Blade 514 can be an iron armature with permanent magnets 508a, 508b at the two ends. Magnets 508a, 508b can be, for example, low gauss, rare earth magnets. Valve 202 can further include a keyway 520 for alignment between blade 514 and sleeve 506. In some embodiments, a Hall-effect sensor 510 can be placed at one end of sleeve 506 to determine and verify whether valve 202 is in the open state or the closed state.

Valve 202 can be opened or closed by changing the relative position of blade 514 inside sleeve 506. When blade 514 is at a position so that the two orifices 512, 516 coincide, valve 202 is open. Otherwise, valve 202 is closed. To close valve 202, electromagnets 502a, 502b are polarized briefly, for example, a 100 milliseconds pulse at 20 milliamp. The magnetic field created by the electromagnets 502a, 502b can pull blade 514 in one direction, for example, in the direction of arrow 518a, until blade 514 contacts plate 512a. When this happens, blade 514 is locked to plate 512a because of the attraction between magnet 508a and steel plate 512a. The electromagnets 502a, 502b do not need to be polarized further for blade 514 to remain in its position.

To open valve 202, electromagnets 502a, 502b can be reverse polarized, pulling blade 514 in the direction of arrow 518b. This pulling force can be sufficiently high in order to overcome the attraction between magnet 508a and steel plate 512a. Blade 514 then moves in the direction of arrow 518b, and locks to plate 512b because of the attraction between magnet 508b and steel plate 512b.

In some embodiments, blade 514 can be moved in the direction of arrows 518a, 518b by a magnetic field created by an external source (not shown), so that valve 202 can be manually opened or closed in case of a device failure. This feature may also be used to unclog valve 202 when blade 514 is moved back and forth rapidly.

Various components of valve 202, including sleeve 506 and blade 514, can be made from or coated with a biocompatible, self-lubricating material, for example a Teflon™ type material. The Teflon™ material will reduce friction and clogging inside valve 202. Valve 202 can be, for example, 7 mm long and have a diameter of 1.5 mm. Orifices 512, 516 can have, for example, a diameter of 0.025 inch or larger. This relatively large orifice size can reduce the likelihood of valve clogging.

Figure 5B:
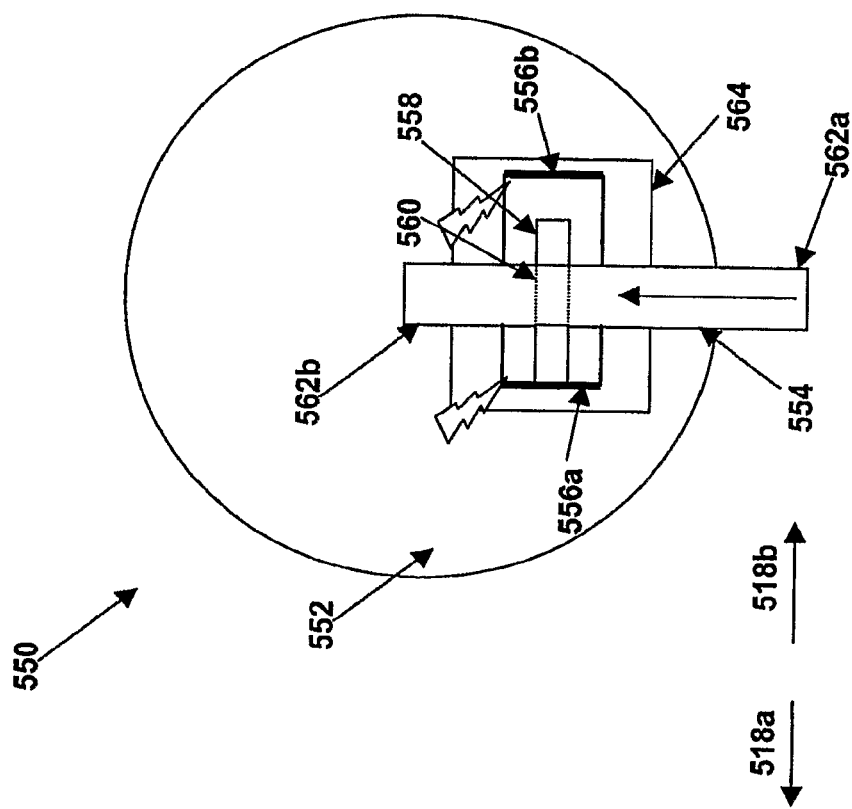
FIG. 5*b* is a top view depicting an electromagnetic valve, according to various embodiments of the present invention.

FIG. 5b is a top view illustrating an electromagnetic valve 550 of various embodiments of the present invention. Valve 550 includes a conduit 554 and a valve case 564 which includes a permanent magnet 558 and two stop plates 556a and 556b. One end 562a of conduit 554 can be placed, for example, in the anterior chamber of an eye. The other end 562b of conduit 554 can be connected to a drainage plate 552. Permanent magnet 558 has an orifice 560 (shown in phantom lines) that permits fluid to pass through valve 550 from one end 562a of conduit 554 to the other end 562b onto drainage plate 552 when magnet 558 is in an open position (as shown).

Stop plates 556a and 556b are made of a ferrous material. Stop plates 556a and 556b limit movement of magnet 558 and serve to hold magnet 558 in either the open position or a closed position. Coils (not shown) around the ends of valve case 564 can create a temporary magnetic field (shown as lightning bolts) to drive permanent magnet 558 in the direction of arrow 518a or arrow 518b to either the open or the closed position. In the closed position, the body of magnet 558 blocks the passage of fluid. Magnet 558 can include a keyway (not shown) so that magnet 558 is properly aligned with valve case 564, and/or a groove (not shown) to release the pressure of air trapped by the magnet's movements. Valve 550 can also be designed so that magnet 558 can be driven to move in directions perpendicular to drainage plate 552, which can facilitate the use of an external magnet (not shown) to open or close valve 550 when there is a failure of the electromagnetic system.

The present invention is not limited to the used of valves as described above. Other types of valves can be used, including but not limited to reed valves and valves having a rotating cam or blade. In some embodiments, instead of having only an open state and a closed state, a valve can have multiple open states, releasing fluids at different rates. This can be achieved, for example, by exposing orifices having varying sizes, as described below in connection with FIGS. 12 and 13.

Control device 208, shown in FIG. 2, can be coupled with sensor 206 and valve 202. Control device 208 can be implemented in an Application Specific Integrated Circuit ("ASIC"), a microprocessor, a microcontroller, or other similar devices. When implemented in a microprocessor or microcontroller, for example, control device 208 can run software programs for controlling system 118. Control device 208 can be configured to receive pressure and/or temperature measurements from sensor 206 using an Input/Output ("I/O") port. Control device 208 also can include other I/O ports for power control of sensor 206, and/or power control of other sensors, for example, a Hall-effect sensor for verifying valve state. In addition, control device 208 may include other I/O ports for monitoring and/or recharging the battery, and/or for controlling valve 202 (e.g., polarizing electromagnets in valve 202).

In some embodiments, control device 208 includes I/O ports for wireless communication with external devices. Control device 208 may further include circuits to demodulate signals received from various I/O ports and to convert the signals into digital signals. Control device 208 may transmit the various signals, for example, digital signals containing pressure measurements, to external devices for monitoring purposes. Control device 208 can run, for example, on 5.8 milliamp current at 25 Mhz.

Figure 6:
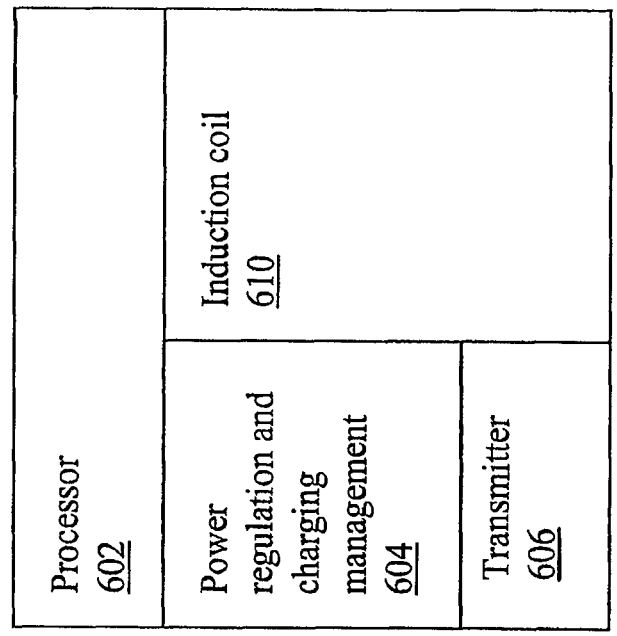
FIG. 6 is a block diagram illustrating the layout of an electronic control device, according to various embodiments of the present invention.

FIG. 6 is a block diagram illustrating an example of the electronics layout of control device 208. As shown, control device 208 can include a processor 602 that performs logic operations for valve control (e.g., logic operations described below in connection with FIGS. 11 and 12), or any other logic operations for controlling the operation of system 118. Control device 208 can include a power regulation and charging management module 604 for regulating power supply to various components of system 118 (shown in FIG. 2) and managing the recharging of a battery (not shown). In addition, control device 208 can include a transmitter 606 for wireless communication with external devices (not shown), and an induction coil 610 for recharging the battery.

Figure 7:
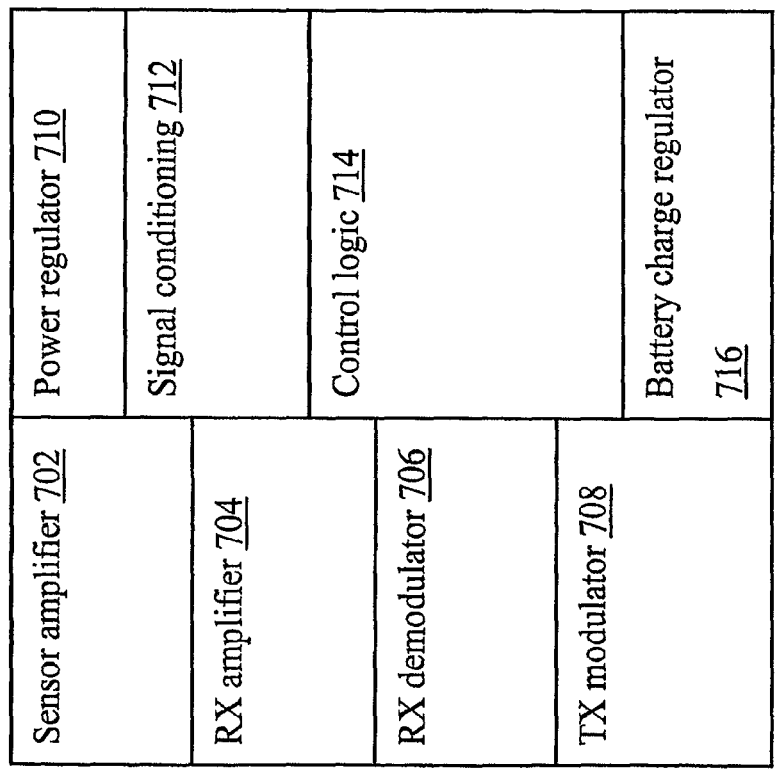
FIG. 7 is a block diagram illustrating the layout of an electronic control device, according to various embodiments of the present invention.
Figure 8:
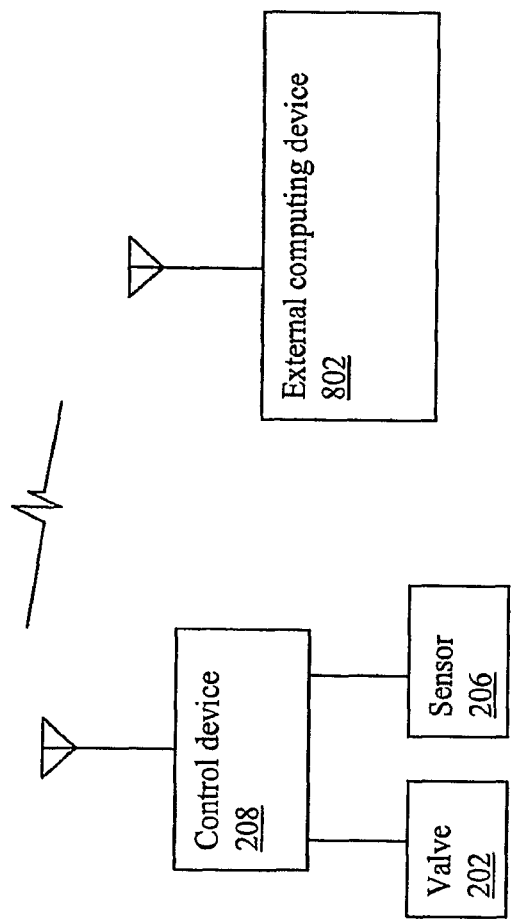
FIG. 8 is a block diagram depicting a pressure control system and an external computing device, according to various embodiments of the present invention.

FIG. 7 is a block diagram illustrating another example of the electronics layout of control device 208. As shown, control device 208 can include a sensor amplifier 702 for amplifying signals from sensor 206 (shown in FIG. 2). Control device 208 can include transceiver components such as RX amplifier 704 for amplifying received radio frequency ("RF") signals, RX demodulator 706 for demodulating received RF signals, and TX modulator 708 for modulating RE signals to be transmitted. Control device 208 also can include power regulator 710 for regulating power supply to various components of system 118 (shown in FIG. 2), and battery charge regulator 716 for regulating the recharging of a battery (not shown). In addition, control device 208 can include control logic circuit 714, which can perform logic operations for valve control (e.g., logic operations described below in connection with FIGS. 11 and 12), or any other logic operations for controlling the operation of system 118. Control device 208 also can include logic signal conditioning circuit 712, which may include amplification and filtering components.

Using wire-bonding techniques well known in the art, wires can be attached to electrodes on transducer 300, connecting transducer 300 with control device 208. Wires can be coated with TEFLON™ non-stick materials for electrical isolation. Transducer 300 can be controlled by control device 208 to take pressure measurements repeatedly, and the time intervals between consecutive measurements can be optimized for less power consumption.

In some embodiments, the wireless connection between control device 202 and computing device 802 can be provided by a magnetically coupled, low frequency differential FM system utilizing multiple sub-carriers, capable of two-way communication. Alternatively, the wireless connection can be provided by other kinds of wireless communication mechanisms well known in the art, including, but not limited to, infrared light, visible light, and/or microwave communication systems.

Computing device 802 can be, for example, a laptop computer, a desktop computer, a Personal Digital Assistant ("PDA"), or a specialized data acquisition and control device. Software running on computing device 802 can be used to record different types of data received from control device 208. Data can be stored on a hard disk for future retrieval, analysis, conversion, and/or display. Software can also be used to control implanted system 118. For example, the software may send control commands to control device 208 (e.g., a signal to turn on device 208). The software may also send parameters (e.g. pressure set points) and/or software programs used by control device 208 in controlling valve 202.

Figure 9:
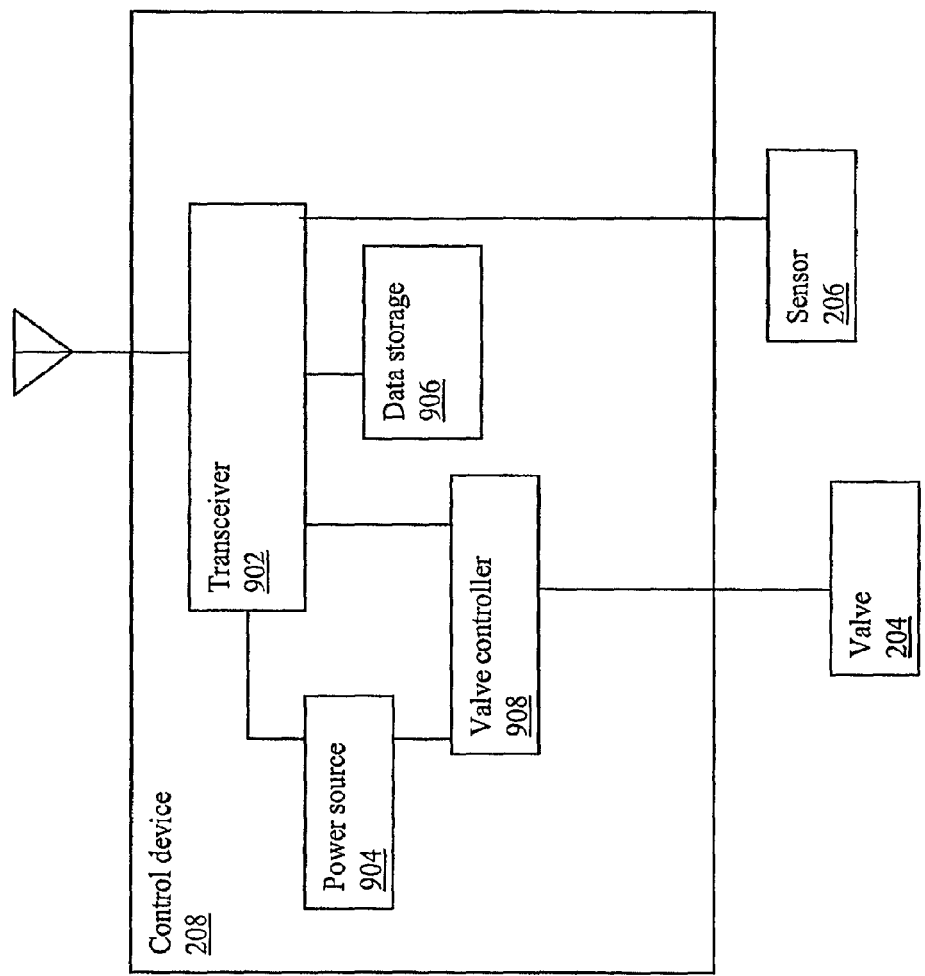
FIG. 9 is a block diagram depicting a pressure control system, according to various embodiments of the present invention.

FIG. 9 is a block diagram that illustrates control device 208 of various embodiments of the present invention. As shown, control device 208 can include, but not limited to, a transceiver 902, a power source 904, a valve controller 908, and data storage 906. Data storage 906 can, for example, contain 1 kilobyte of memory, and can store different types of information. For example, pressure measurements obtained by sensor 206, system power information sent by power source 904, and/or valve state information can be stored. A compression algorithm can be used to permit storage of measurement data collected over long periods of time. The information can also be transmitted to an external computing device, for example, computing device 802 in FIG. 8, through transceiver 902. In some embodiments, control device 208 does not transmit any data during normal operation, but an external device 802 may request a data transmission. Data storage 906 may also contain non-volatile memory, which can be used to store parameters and/or programs used for valve control and/or other purposes.

Figure 10:
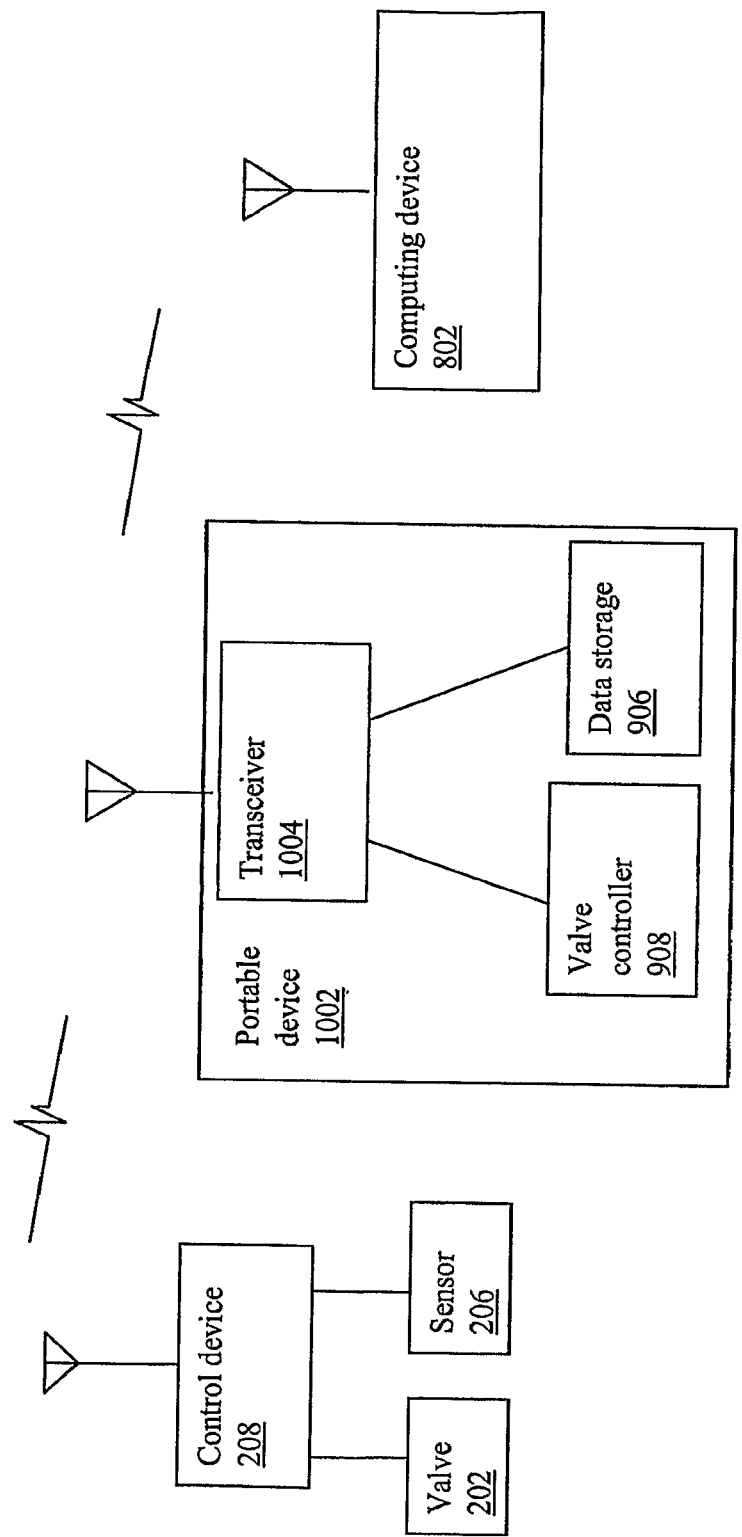
FIG. 10 is a block diagram depicting a pressure control system, according to various embodiments of the present invention.

FIG. 10 is a block diagram illustrating another pressure control system of various embodiments of the present invention. Different from the system in FIG. 9, a portable device 1002, which is an external device that can be carried with the patient, contains valve controller 908 and data storage 906. Portable device 1002 can communicate with control device 208 and external computing device 802 through transceiver 1004. External computing device 802 can be located at a remote location, under the monitoring of a physician. Alternatively, portable device 1002 and/or external computing device 802 can send information received from control device 208 to a remote location through a communications network, for example, the Internet. In some embodiments, the functions provided by valve controller 908 and data storage 906 can be included in the external computing device 802, eliminating the need for portable device 1002. Valve 202 and sensor 206 can be separated (as shown) or attached together, depending on the various applications the pressure control system is used.

The following describes methods of monitoring and controlling pressure of a body part (e.g., IOP). In particular, various methods of the present invention are described in connection with system 118 depicted in FIGS. 1 and 2. System 118 releases pressure by draining fluids in the body part (e.g., aqueous humor in anterior chamber 102), using valve 202. In some embodiments, control device 208 controls valve 202 according to a single set point. When pressure rises above the set point, control device 208 can open valve 202. Fluids then passes through tube 116 and valve 202, due to a pressure difference between the two sides of valve 202, releasing pressure inside the body part (e.g., anterior chamber 102). With respect to IOP, the pressure difference varies depending upon the pressure inside anterior chamber 102, which in a normal individual is 10-15 mm Hg. When pressure falls below the set point, control device 208 can close valve 202. Therefore, pressure is maintained at the set point.

Figure 11:
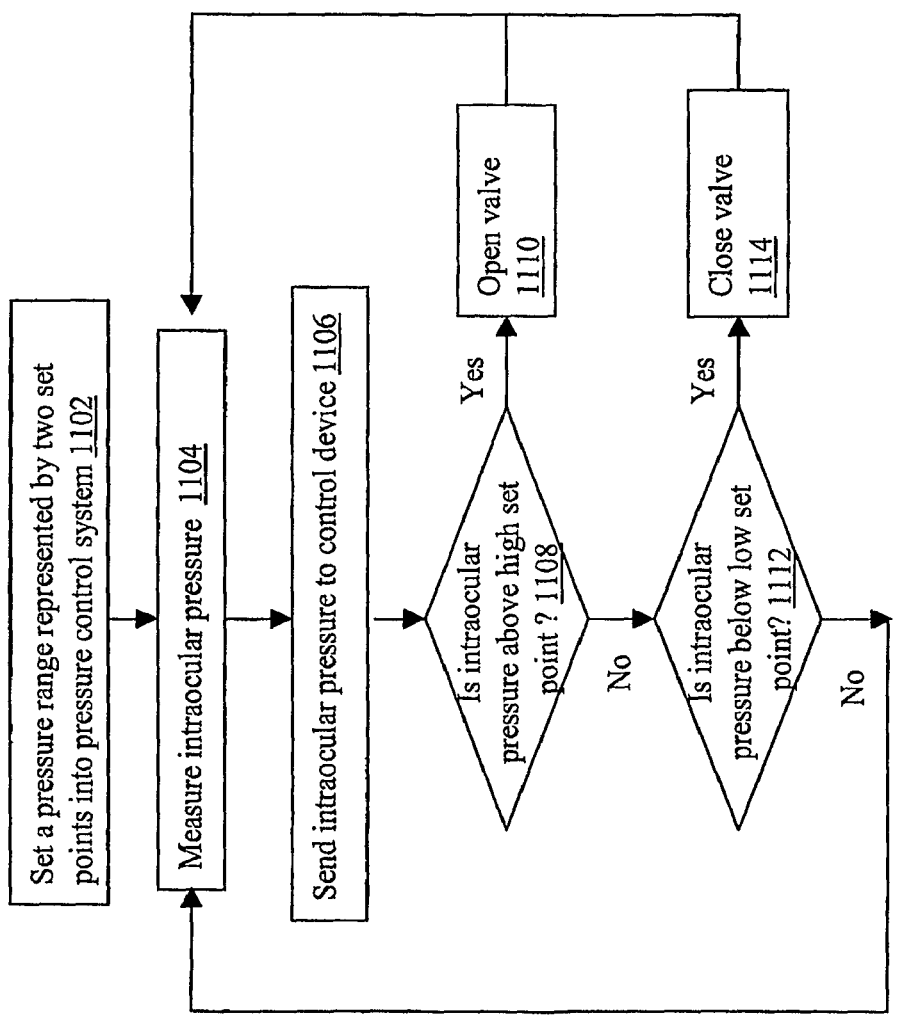
FIG. 11 is a flow chart illustrating the operation of a pressure control system, according to various embodiments of the present invention.

Alternatively, as illustrated by the flow chart in FIG. 11, pressure control system 118 of various embodiments of the present invention can be used to maintain pressure of a body part within a pressure range. At 1102, the pressure range, represented by a low set point and a high set point, can be set into system 118. At 1104, sensor 206 of the implanted system 118 measures the pressure of a body part (e.g., IOP in the anterior chamber 102 of the patient's eye). At 1106, this pressure measurement is sent to control device 208. At 1108, the control device 208 compares the measurement to the high set point. If pressure exceeds the high set point, valve 202 of the system opens at 1110, and fluids is drained from the body part. Otherwise, the control device 208 compares the measurement to the low set point at 1112. If pressure is below the low set point, valve 202 closes at 1114. If not, pressure of the body part is within the pressure range, and therefore system 118 does not change the state of valve 202. System 118 then repeats the cycle starting from 1104 within a predetermined period of time.

Various components of valve 202, including sleeve 506 and blade 514, can be made from or coated with a biocompatible, self-lubricating material, for example a TEFLON™ non-stick type material. The TEFLON™ non-stick material will reduce friction and clogging inside valve 202. Valve 202 can be, for example, 7 mm long and have a diameter of 1.5 mm. Orifices 512, 516 can have, for example, a diameter of 0.025 inch or larger. This relatively large orifice size can reduce the likelihood of valve clogging.

Figure 12:
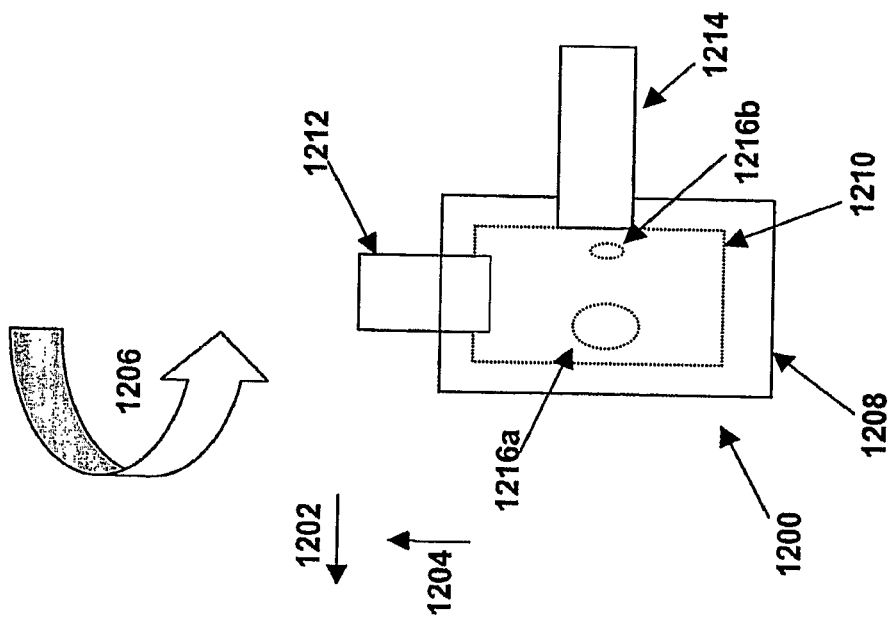
FIG. 12 is a cross-sectional view of a cylindrical valve, according to various embodiments of the present invention.

In some embodiments, a valve used in pressure control system 118 can have more than one open state, capable of releasing fluids (e.g., aqueous humor) at different rates. An example of such a valve is illustrated in FIG. 12, which is a cross-sectional view of a cylindrical valve generally at 1200. Valve 1200 includes an inner chamber 1210 that can rotate in the direction of arrow 1206 inside an outer wall 1208. An inlet tube 1214 and an outlet tube 1212 extend through wall 1208 to reach chamber 1210. A plurality of orifices of varying sizes, for example, orifices 1216a and 1216b, are located on the wall of chamber 1210. When one or more of the orifices (e.g., 1216a, 1216b) are aligned with inlet tube 1214, fluids can flow into inner chamber 1210 can out of outlet tube 1212, thereby releasing pressure. Depending on the size of the orifice that is aligned with inlet tube 1214, fluids can be released at different rates.

Figure 13:
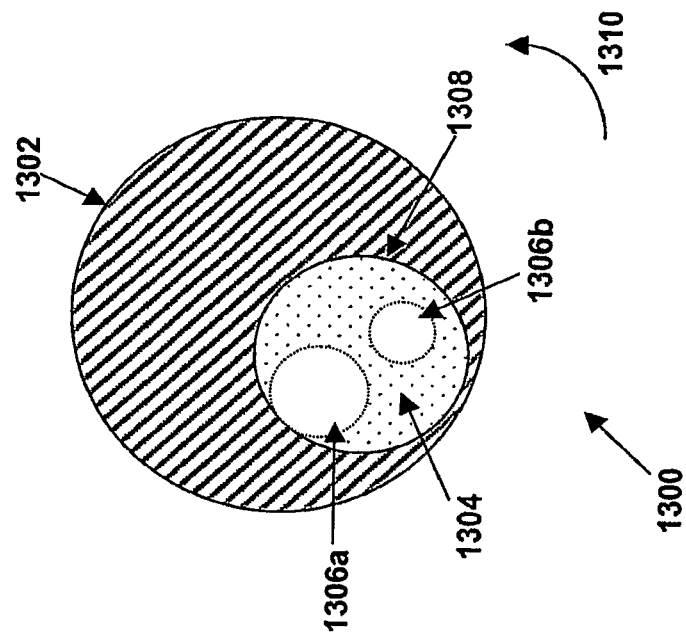
FIG. 13 is a top view depicting portions of a valve, according to various embodiments of the present invention.

FIG. 13 is a diagram illustrating portions of a valve 1300 of another embodiment of the present invention. Valve 1300 includes a top plate 1302 having an orifice 1308, and a bottom plate 1304 having a plurality of orifices (e.g., 1306a, 1306b) with varying sizes. When top plate 1302 rotates in the direction of arrow 1310, one or more of orifices (e.g., 1306a, 1306b) on bottom plate 1304 can be aligned with orifice 1308 on the top plate. Therefore, valve 1300 can also be used to release fluids (e.g., aqueous humor) at different rates.

Using valves such as 1200 and 1300, finer control of pressure (e.g., IOP) can be achieved. In addition, while an orifice (e.g., 1216a in FIG. 12) in a valve can be used to increase the flow capacity of the valve, it may also be used to permit a drug to be administered. For example, an orifice (e.g., 1216a) can be connected with a pump (not shown) that delivers drugs into the body part from an implanted drug reservoir (not shown).

Figure 14:
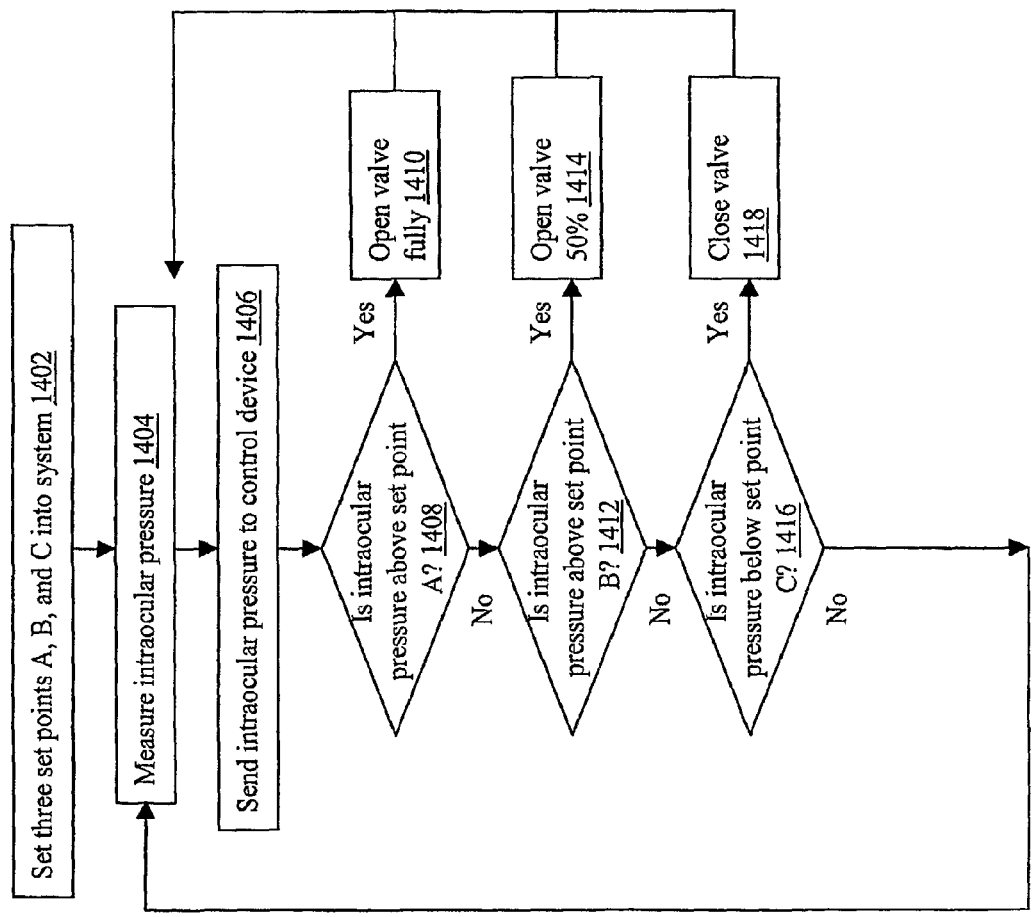
FIG. 14 is a flow chart illustrating the operation of a pressure control system, according to various embodiments of the present invention.

FIG. 14 is a flow chart illustrating the operation of a pressure control system 118 using such a valve that have more than one open state, according to various embodiments of the present invention. At 1402, three set points, A, B, and C, with A greater than B and B greater than C, are set into system 118. At 1404, sensor 206 of the implanted system 118 measures the pressure of a body part (e.g., IOP in the anterior chamber 102 of the patient's eye). At 1406, this pressure measurement is sent to control device 208. At 1408, the control device 208 compares the measurement with set point A. If pressure is above set point A, valve 202 of the system can open fully at 1410, allowing fluids to be drained at the highest rate. Otherwise, control device 208 compares the measurement with set point B at 1412. If pressure is above set point B, valve 202 can open partially (e.g., 50%) at 1414. If not, control device 208 compares the measurement with set point C at 1416. If pressure is below set point C, valve 202 closes at 1418. Therefore, system 118 can drain the body part at different rates when pressure falls within different ranges.

Although embodiments of the present invention are described in connection with monitoring and controlling intraocular pressure, they may also be used for other applications. For example, embodiments of the present invention can be used to monitor and control intracranial, intraspinal, and/or inner ear pressure by releasing fluid in a skull, a spinal cord, or an inner ear to outside drains or internal passages. Embodiments of the present invention can also be used to control pressure in blood steams, or to permit or restrict access to surgical anastomoses, which in many situations can suffer from acute or chronic edema or excessive or restricted (e.g., ischemic) blood flow conditions. Additionally, embodiments of the present invention can detect infiltration of IV lines. For example, a pressure sensor can be placed inline with an IV line. If the pressure differential becomes smaller, the pressure control system can indicate increased resistance caused by fluid being forced into the tissue rather than the low resistance venous pathway.

In combination with an implanted pump, embodiments of the present invention can be used to control drug delivery. For example, based on the pressure measurements obtained by a pressure sensor, the system can open a valve to release drugs held in an internal or external reservoir into a patient. In addition, opening of a valve can be based on temperature, heart rate, blood pressure or other fluid pressure limits recognized by the system. Application of such a system may include hypertensive crises requiring addition of sodium nitroprusside or other fast acting agents; addition of agents to control cardiac arrhythmias or to respond to a reduction in blood pressure due to heart failure. The present invention can also be used for other general applications in animals, plants, and/or mechanical devices where changes in pressure need to be monitored and/or controlled in a low pressure, low flow environment. MEMS technology can be used in various components of the pressure control system, including but not limited to drug reservoir, valve, and/or components providing computational and control function.

Other embodiments, extensions, and modifications of the ideas presented above are comprehended and within the reach of one skilled in the art upon reviewing the present disclosure. Accordingly, the scope of the present invention in its various aspects should not be limited by the examples and embodiments presented above. The individual aspects of the present invention, and the entirety of the invention should be regarded so as to allow for modifications and fixture developments within the scope of the present disclosure.

The invention claimed is:

1. A system for controlling pressure in a body part, comprising:
 an implantable tube, having a first open end and a second open end, the first open end configured to be disposed in a body part;
 an implantable valve coupled to the second open end of the tube and having at least one open state and a closed state wherein the valve further comprises an implantable sleeve having first and second ends and having an orifice extending through a wall of the sleeve, and a blade positioned inside said sleeve, and formed at least in part from a material that is reactive to magnetic force, the blade configured to slide from a first position relative to the sleeve where the blade does not block the orifice and the valve is in the at least one open state, to a second position relative to the sleeve where the blade blocks the orifice and the valve is in at least one closed state, such that a position of the blade relative to the sleeve determines whether the valve is in the at least one open state or the closed state;

a first implantable sensor for actively obtaining at least one measurement of pressure within the body part; and an implantable control device electrically coupled with the valve and the sensor, for receiving the at least one measurement and switching the valve between the at least one open state and the closed state based on the at least one measurement, wherein the tube is configured to drain fluids from the body part when the valve is in the at least one open state, due to a difference of pressure between the first and the second open end of the tube, the difference created by native differences in pressure of the body part to another body part.

2. The system of claim 1, wherein the sensor comprises a piezoresistive transducer.

3. The system of claim 1, wherein the sensor comprises a fiber optic sensor.

4. The system of claim 1, wherein the valve can be switched between the at least one open state and the closed state by an external magnet or piezoelectric device.

5. The system of claim 1, wherein the valve comprises at least one electromagnet, and the control device switches the valve between the at least one open state and the closed state by polarizing the at least one electromagnet.

6. The system of claim 5, wherein the valve further comprises:
the implantable blade having a first magnetic end and a second magnetic end, and
a second implantable sensor for verifying the position of the blade.

7. The system of claim 1, wherein the valve comprises a rotating member having one or more orifices.

8. The system of claim 1, wherein the control device comprises a wireless communication module for transmitting information to an external device.

9. The system of claim 1, wherein the control device comprises a two-way wireless communication module for transmitting and receiving information to and from an external device.

10. The system of claim 9, wherein the control device switches the valve between the at least one open state and the closed state according to at least one set point, the at least one set point being configurable by the external device.

11. The system of claim 1, wherein the control device comprises:
a battery; and
an electromagnetic induction system configured to recharge the battery.

12. The system of claim 1, wherein the sensor is further configured to obtain a temperature measurement, and the control device is further configured to receive the temperature measurement and switch the valve based on the pressure and the temperature measurements.

13. The system of claim 1, wherein the valve has at least two open states and drains fluids within a body part at different rates in different open states.

14. The system of claim 1, further comprising an implantable pump configured to deliver drugs into the body part.

15. The system of claim 1, wherein the control device further comprises a power source.

16. The system of claim 1, wherein the body part is an eye.

17. A system for controlling pressure in a body part, comprising:
an implantable tube, having a first open end and a second open end, the first open end configured to be disposed in a body part;

an implantable valve coupled to the second open end of the tube and having at least one open state and a closed state wherein the valve further comprises an implantable sleeve having first and second ends made from a material that is reactive to magnetic force and having an orifice extending through a wall of the sleeve, and a blade positioned inside said sleeve, and formed at least in part from a material that is reactive to magnetic force, the blade configured to slide from a first position relative to the sleeve where the blade does not block the orifice and the valve is in the at least one open state, to a second position relative to the sleeve where the blade blocks the orifice and the valve is in at least one closed state, such that a position of the blade relative to the sleeve determines whether the valve is in the at least one open state or the closed state;

a first implantable sensor for actively obtaining at least one measurement of pressure within the body part; and an implantable control device electrically coupled with the valve and the sensor, for receiving the at least one measurement and switching the valve between the at least one open state and the closed state based on the at least one measurement, wherein the tube is configured to drain fluids from the body part when the valve is in the at least one open state, through use of an implantable pump in the device.

18. The system of claim 17, wherein the valve can be switched between the at least one open state and the closed state by an external magnet or piezoelectric device.

19. The system of claim 17, wherein the valve comprises at least one electromagnet, and the control device switches the valve between the at least one open state and the closed state by polarizing the at least one electromagnet.

20. The system of claim 19, wherein the valve further comprises:
the implantable blade having a first magnetic end and a second magnetic end, and
a second implantable sensor for verifying the position of the blade.

21. The system of claim 17, wherein the control device comprises:
a battery; and
an electromagnetic induction system configured to recharge the battery.

22. The system of claim 17, wherein the control device further comprises a power source.

23. The system of claim 17, wherein the body part is an eye.

24. A system for controlling pressure in a body part, comprising:
an implantable tube, having a first open end and a second open end, the first open end configured to be disposed in a body part;

an implantable valve coupled to the second open end of the tube and having at least one open state and a closed state;

wherein the valve comprises an implantable sleeve having a first and second opening;

wherein the valve further comprises a blade, comprised at least in part of a material reactive to magnetic force, and positioned inside said sleeve and configured to move relative to the sleeve, such that a position of the blade determines whether the valve is in the at least one open state or the closed state;

a first implantable sensor for actively obtaining at least one measurement of pressure within the body part; and an implantable control device electrically coupled with the valve and the sensor, for receiving the at least one measurement and switching the valve between the at least one open state and the closed state based on the at least one measurement, wherein the tube is configured to drain fluids from the body part when the valve is in the at least one open state, through use of an implantable pump in the device.

25. The system of claim 24, wherein the body part is an eye.

26. A system for controlling pressure in a body part, comprising:

an implantable tube, having a first open end and a second open end, the first open end configured to be disposed in a body part;

an implantable valve coupled to the second open end of the tube and having at least one open state and a closed state;

wherein the valve comprises an implantable sleeve having a first and second opening;

wherein the valve further comprises a blade, comprised at least in part of a material reactive to magnetic force, and positioned inside said sleeve and configured to move relative to the sleeve, such that a position of the blade determines whether the valve is in the at least one open state or the closed state;

a first implantable sensor for actively obtaining at least one measurement of pressure within the body part; and an implantable control device electrically coupled with the valve and the sensor, for receiving the at least one measurement and switching the valve between the at least one open state and the closed state based on the at least one measurement, wherein the tube is configured to drain fluids from the body part when the valve is in the at least one open state, due to a difference of pressure between the first and the second open end of the tube, the difference created by native differences in pressure of the body part to another body part.

27. The system of claim 26, wherein the body part is an eye.

* * * * *